United States Patent
Palushi et al.

(10) Patent No.: US 11,147,629 B2
(45) Date of Patent: Oct. 19, 2021

(54) SURGICAL NAVIGATION SYSTEM WITH AUTOMATICALLY DRIVEN ENDOSCOPE

(71) Applicant: Acclarent, Inc., Irvine, CA (US)

(72) Inventors: Jetmir Palushi, Irvine, CA (US); Itzhak Fang, Irvine, CA (US); William J. Kane, Newport Coast, CA (US); David A. Smith, Jr., Lake Forest, CA (US)

(73) Assignee: Acclarent, Inc., Irvine, CA (US)

( * ) Notice: Subject to any disclaimer, the term of this patent is extended or adjusted under 35 U.S.C. 154(b) by 506 days.

(21) Appl. No.: 16/003,434

(22) Filed: Jun. 8, 2018

(65) Prior Publication Data

US 2019/0374288 A1    Dec. 12, 2019

(51) Int. Cl.
*A61B 34/20* (2016.01)
*A61B 1/00* (2006.01)
(Continued)

(52) U.S. Cl.
CPC ............ *A61B 34/20* (2016.02); *A61B 1/0016* (2013.01); *A61B 1/00045* (2013.01); *A61B 1/00183* (2013.01); *A61B 1/04* (2013.01); *A61B 5/062* (2013.01); *A61B 6/032* (2013.01); *A61B 1/233* (2013.01); *A61B 2034/2051* (2016.02); *A61B 2090/3762* (2016.02)

(58) Field of Classification Search
CPC combination set(s) only.
See application file for complete search history.

(56) References Cited

U.S. PATENT DOCUMENTS

| | | |
|---|---|---|
| 5,792,135 A | 8/1998 | Madhani et al. |
| 5,817,084 A | 10/1998 | Jensen |

(Continued)

FOREIGN PATENT DOCUMENTS

| | | |
|---|---|---|
| EP | 3108796 A1 | 12/2016 |
| JP | 3618413 B2 | 2/2005 |

(Continued)

OTHER PUBLICATIONS

U.S. Appl. No. 15/695,520, entitled "Sensor Guided Instrument with Penetrating Feature," filed Sep. 5, 2017.

(Continued)

*Primary Examiner* — John P Leubecker
*Assistant Examiner* — Shankar Raj Ghimire
(74) *Attorney, Agent, or Firm* — Frost Brown Todd LLC (57) ABSTRACT

A surgical navigation system includes an endoscope having a body, a shaft having a distal shaft end, an optical conduit, and a moveable optical element. The moveable optical element is configured to provide a field of view defining a line of sight, and is operable to capture an image within the field of view. The system further includes a drive mechanism operable to move the movable optical element to adjust a direction of the line of sight, a navigation sensor operable to generate a signal corresponding to a location of the distal shaft end within a patient, and a processor. The processor is operable to determine a location of the distal shaft end within the patient based on the signal, and command the drive mechanism to position the movable optical element so the line of sight is directed toward a selected point of interest within the patient.

20 Claims, 5 Drawing Sheets

(51) Int. Cl.
*A61B 5/06* (2006.01)
*A61B 1/233* (2006.01)
*A61B 1/04* (2006.01)
*A61B 6/03* (2006.01)
*A61B 90/00* (2016.01)

(56) References Cited

U.S. PATENT DOCUMENTS

| | | | |
|---|---|---|---|
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,783,524 B2 | 8/2004 | Anderson et al. | |
| 7,524,320 B2 | 4/2009 | Tierney et al. | |
| 7,691,098 B2 | 4/2010 | Wallace et al. | |
| 7,720,521 B2 | 5/2010 | Chang et al. | |
| 7,806,891 B2 | 10/2010 | Nowlin et al. | |
| 7,809,421 B1* | 10/2010 | Govari | A61B 5/062 600/407 |
| 8,123,722 B2 | 2/2012 | Chang et al. | |
| 8,190,389 B2 | 5/2012 | Kim et al. | |
| 8,320,711 B2 | 11/2012 | Altmann et al. | |
| 8,479,969 B2 | 7/2013 | Shelton, IV | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,702,626 B1 | 4/2014 | Kim et al. | |
| 8,783,541 B2 | 7/2014 | Shelton, IV et al. | |
| 8,800,838 B2 | 8/2014 | Shelton, IV | |
| 8,820,605 B2 | 9/2014 | Shelton, IV | |
| 8,844,789 B2 | 9/2014 | Shelton, IV et al. | |
| 9,167,961 B2 | 10/2015 | Makower et al. | |
| 9,198,736 B2 | 12/2015 | Kim et al. | |
| 9,301,759 B2 | 4/2016 | Spivey et al. | |
| 9,808,144 B2 | 11/2017 | Goldfarb et al. | |
| 2002/0022767 A1* | 2/2002 | Dohi | G02B 5/06 600/173 |
| 2005/0182295 A1* | 8/2005 | Soper | A61B 1/00172 600/117 |
| 2006/0276686 A1* | 12/2006 | Tsuji | A61B 34/20 600/117 |
| 2007/0208252 A1 | 9/2007 | Makower | |
| 2008/0287783 A1* | 11/2008 | Anderson | A61B 6/12 600/429 |
| 2010/0030031 A1* | 2/2010 | Goldfarb | A61B 1/00183 600/163 |
| 2010/0217075 A1* | 8/2010 | Shigeta | A61B 1/04 600/104 |
| 2011/0004057 A1 | 1/2011 | Goldfarb et al. | |
| 2011/0060214 A1 | 3/2011 | Makower | |
| 2013/0317339 A1 | 11/2013 | Waldstreicher et al. | |
| 2014/0121459 A1* | 5/2014 | Hoeg | A61B 1/00174 600/109 |
| 2014/0187916 A1* | 7/2014 | Clark | A61B 5/6852 600/424 |
| 2014/0200444 A1 | 7/2014 | Kim et al. | |
| 2014/0364725 A1 | 12/2014 | Makower | |
| 2016/0008083 A1 | 1/2016 | Kesten et al. | |
| 2016/0310042 A1 | 10/2016 | Kesten et al. | |
| 2016/0360120 A1* | 12/2016 | Inoue | A61B 1/00071 |
| 2017/0202624 A1* | 7/2017 | Atarot | A61B 17/00234 |
| 2018/0104001 A1 | 4/2018 | Palushi et al. | |
| 2019/0290111 A1* | 9/2019 | Shademan | A61B 1/00165 |
| 2019/0320882 A1* | 10/2019 | Chen | A61B 1/0058 |
| 2019/0335104 A1* | 10/2019 | Sugie | A61B 1/00096 |

FOREIGN PATENT DOCUMENTS

| | | | | |
|---|---|---|---|---|
| WO | WO-2010014421 A1 * | 2/2010 | ......... | G02B 26/0883 |
| WO | WO-2012119694 A1 * | 9/2012 | ......... | A61B 1/00174 |
| WO | WO-2016035359 A1 * | 3/2016 | ......... | A61B 1/00018 |

OTHER PUBLICATIONS

U.S. Appl. No. 15/797,049, entitled "Dilation Catheter with Navigation Sensor and Vent Passageway in Tip," filed Oct. 30, 2017.

U.S. Appl. No. 15/923,164, entitled "Navigation Instrument with obliquely Oriented Sensing Coil," filed Mar. 19, 2018.

U.S. Appl. No. 15/933,737, entitled "Apparatus to Secure Field Generating Device to Chair," filed Mar. 23, 2018.

International Search Report and Written Opinion dated Oct. 4, 2019 for International Application No. PCT/IB2019/054235, 14 pages.

* cited by examiner

SURGICAL NAVIGATION SYSTEM WITH AUTOMATICALLY DRIVEN ENDOSCOPE

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Irvine, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope may be provided in accordance with the teachings of U.S. Pub. No. 2010/0030031, entitled "Swing Prism Endoscope," published Feb. 4, 2010, now abandoned, the disclosure of which is incorporated by reference herein.

Image-guided surgery (IGS) is a surgical technique in which a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MM, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a system display device (e.g., a video monitor) along with an indicator (e.g., cross hairs or an illuminated dot, etc.) showing the real-time position of each surgical instrument relative to the anatomical features shown in the scan images. The scan images and indicator depicted by the system display device are referred to collectively herein as a "navigation image." In this manner, the surgeon is able to know the precise position of each sensor-equipped instrument by viewing the display device even if the surgeon is unable to directly visualize the instrument itself at its current location within the body.

Examples of electromagnetic IGS systems that may be used in ear, nose, and throat (ENT) and sinus surgery include the InstaTrak ENT™ systems available from GE Medical Systems, Salt Lake City, Utah. Other examples of electromagnetic image guidance systems include but are not limited to the CARTO® 3 System by Biosense-Webster, Inc., of Diamond Bar, Calif.; and systems available from Surgical Navigation Technologies, Inc., of Louisville, Colo. An example of an endobronchial instrument that may be used with an IGS system is described in U.S. Pat. Pub. No. 2013/0317339, entitled "Endobronchial Catheter," published Nov. 28, 2013, now abandoned, the disclosure of which is incorporated by reference herein.

When applied to functional endoscopic sinus surgery (FESS), sinus biopsy procedures, balloon sinuplasty, and/or various other ENT procedures, the use of IGS allows the surgeon to achieve more precise movement and positioning of the surgical instruments than can be achieved by viewing through an endoscope alone. This is so because a typical endoscopic image is a spatially limited, 2-dimensional, line-of-sight view. The use of image guidance systems provides a real-time, 3-dimensional view of all of the anatomy surrounding the operative field, not just that which is actually visible in the spatially limited, 2-dimensional, direct line-of-sight endoscopic view. As a result, image guidance systems may be particularly useful during performance of FESS, balloon sinuplasty, and/or various other ENT procedures, especially in cases where normal anatomical landmarks are not present or are difficult to visualize endoscopically.

It may be desirable to provide features that further facilitate the use of an IGS navigation system and associated components in ENT procedures and other medical procedures. While several systems and methods have been made and used with respect to IGS and ENT surgery, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about" and "approximately" for any numerical values or ranges indicate a suitable dimensional tolerance that allows the part or collection of components to function for its intended purpose as described herein.

I. EXEMPLARY SURGICAL NAVIGATION SYSTEM WITH AUTOMATICALLY DRIVEN ENDOSCOPE

As noted above, surgical procedures may be performed using a surgical instrument equipped with a navigation sensor of an IGS navigation system, in combination with an endoscope that provides direct visualization of the surgical instrument and surrounding patient anatomy. This combination of IGS and endoscopy enables the surgeon to more precisely manipulate and view the surgical instrument and anatomy than with IGS or an endoscope alone. In some instances, however, it may be difficult for the surgeon to confirm whether certain anatomical features identified on the navigation image displayed by the IGS navigation system are the same anatomical features being viewed with the endoscope. In other words, it may be difficult to accurately correlate, in real time, an endoscope view with a region of interest in a CT image (or other previously captured image) that is being displayed by an IGS navigation system.

The exemplary surgical navigation system described below incorporates an automatically driven endoscope and IGS components that track a location of a distal end of the endoscope within a patient. A system display depicts the IGS navigation image and allows the surgeon to select a point of interest on the navigation image that corresponds to certain anatomical feature of the patient. The system then controls a drive mechanism coupled with the endoscope to automatically direct a line of sight of the endoscope toward the point of interest indicated by the surgeon. Consequently, the surgeon knows that the anatomical feature being viewed with the endoscope is the same anatomical feature that corresponds to the point of interest specified by the surgeon via the IGS navigation image.

A. Automatically Driven Endoscope

Figure 1:
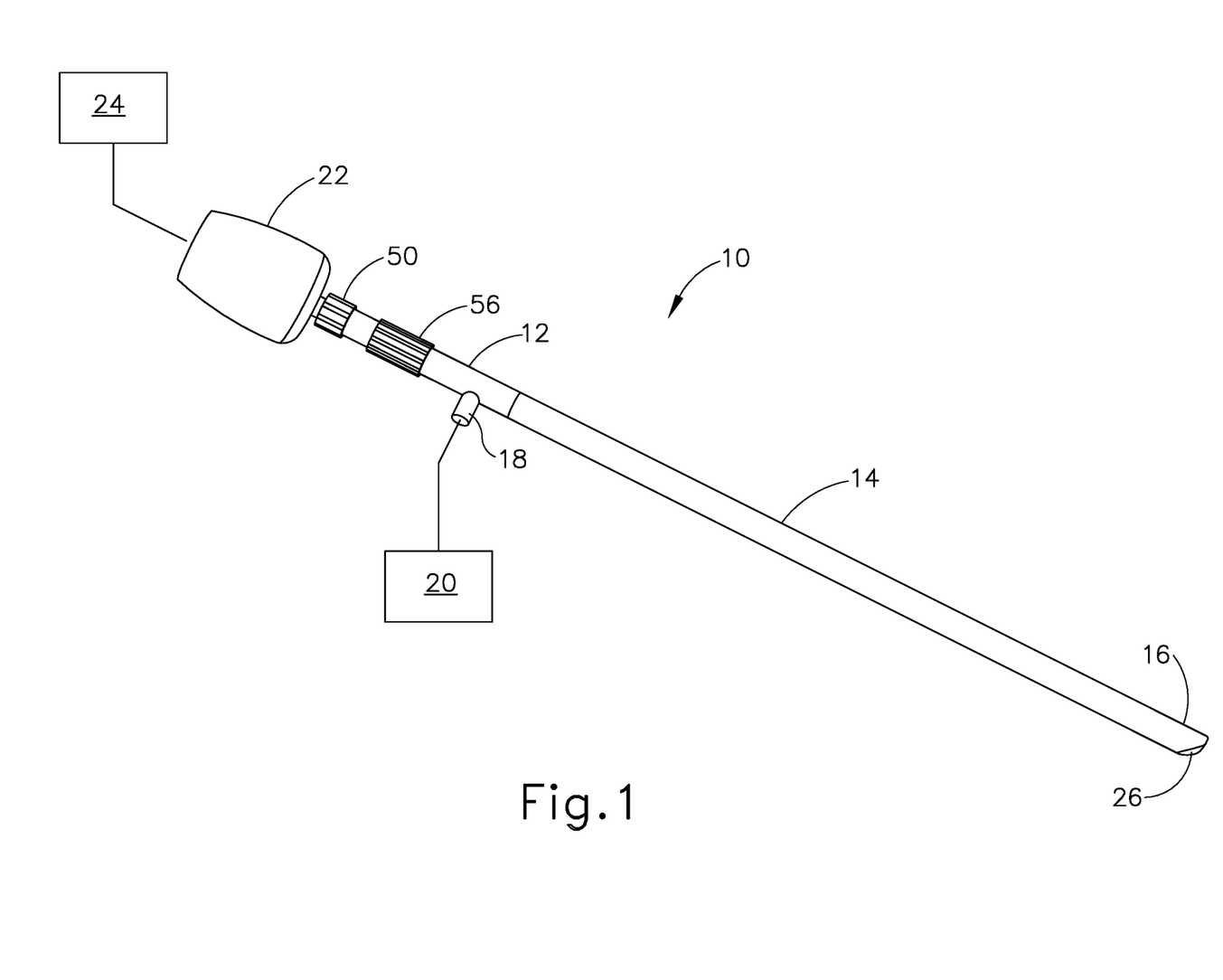
FIG. 1 depicts a perspective view of an exemplary endoscope of a surgical navigation system.
Figure 2:
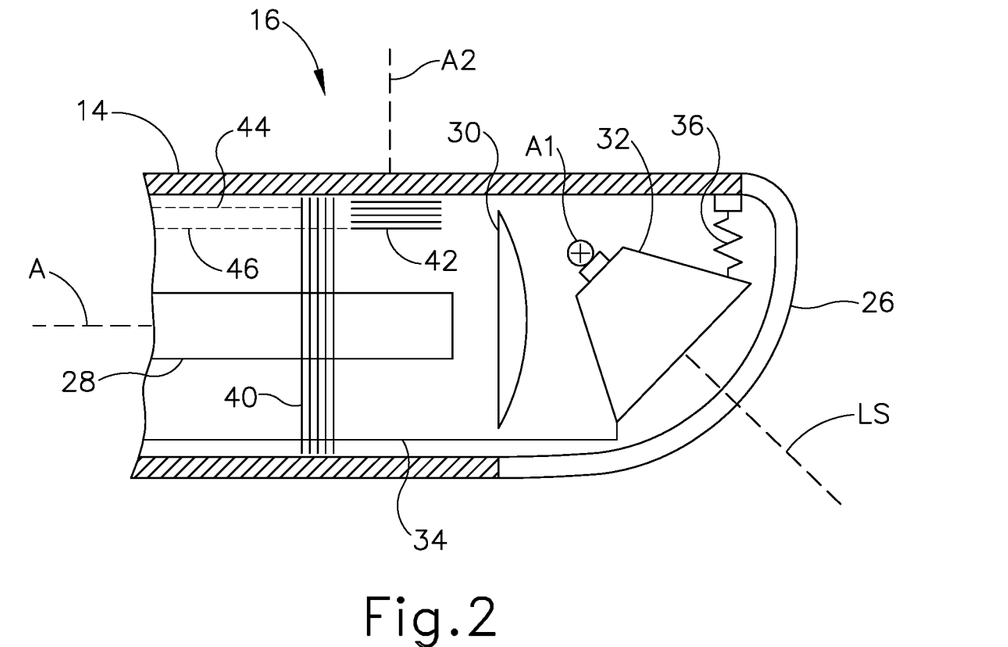
FIG. 2 depicts a schematic side sectional view of the distal end of the endoscope of FIG. 1, showing details of internal components including a swing prism and first and second navigation sensors.
Figure 3:
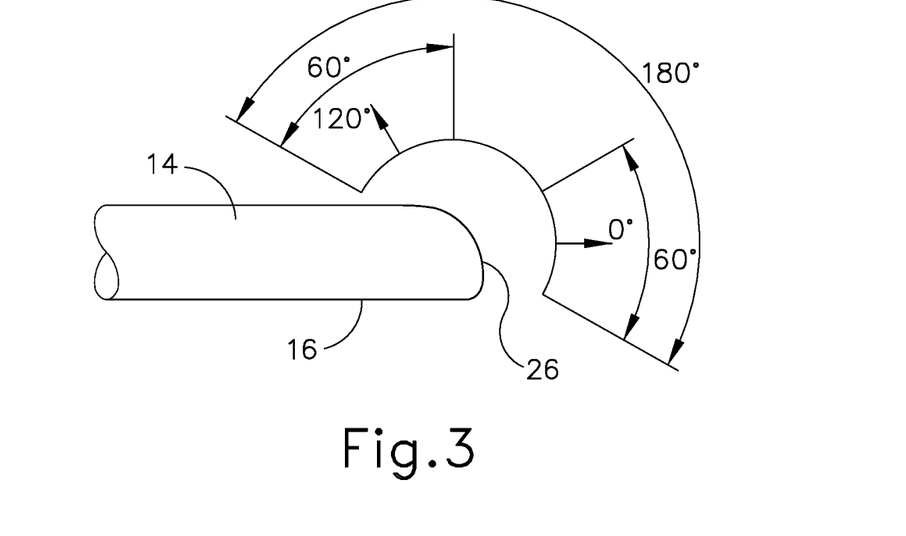
FIG. 3 depicts a schematic side elevational view of a distal end of the endoscope of FIG. 1, showing exemplary viewing ranges of the endoscope.

FIGS. 1-3 show an exemplary endoscope (10) of a surgical navigation system (100), additional components of which are described in greater detail below in connection with FIGS. 5-7. Endoscope (10) of the present example includes a body (12) that may function as a handle, and an elongate rigid shaft (14) that extends distally from body (12) along a longitudinal shaft axis (A) and terminates at a distal shaft end (16) through which an endoscopic image is captured, as described below. In the present example, shaft (14) is rotatable relative to body (12) about shaft axis (A). Endoscope shaft (14) is provided with rounded outer surfaces, thus making shaft (14) atraumatic in use. In one example, shaft (14) may have an outer diameter of approximately 4 mm and a working length of approximately 175 mm.

A distal end of body (12) includes a light source port (18) that projects radially outwardly and communicates with an optical conduit (28) contained within endoscope (10). Alternatively, a light pipe or other light communication feature may be used instead of optical conduit (28) to communicate visible light from light source port (18) to distal shaft end (16). Light source port (18) is configured to connect with a light source (20) that is operable to provide illumination at distal shaft end (16) via optical conduit (28) to enable capturing of an illuminated endoscopic image. An image port (22) is provided at a proximal end of body (12) and is configured to couple with a viewing device (24) that provides visualization of the captured image for a surgeon. Viewing device (24) may be in the form of an eyepiece, a camera, or a display screen, for example.

As shown in FIG. 2, distal shaft end (16) includes a rounded tip having a curved transparent window (26) through which endoscope (10) is configured to capture an image. Optical conduit (28) extends longitudinally through shaft (14) along shaft axis (A) and is configured to optically transmit an image captured through window (26) to image port (22) so the image may be viewed by an operator with viewing device (24). In some examples, optical conduit (28) may be in the form of an optical fiber cable that includes a plurality of image fibers and illumination fibers. In other examples, optical conduit (28) may comprise various other types of optical transmission elements readily apparent to those of ordinary skill in the art in view of the teachings herein. For instance, optical conduit (28) may implement rod lens technology. A self focusing lens (30) is arranged at a distal end of optical conduit (28), proximally of window (26), and is configured to transmit the captured image proximally from a movable optical element (32), described below, to optical conduit (28).

A moveable optical element in the form of a swing prism (32) is arranged within distal shaft end (16) between transparent window (26) and self focusing lens (30). Swing prism (32) is operable to capture an image through window (26) and transmit the image proximally through lens (30) to optical conduit (28). Swing prism (32) is configured to pivot about a pivot axis (A1) that extends transversely to shaft axis (A); and provide endoscope (10) with a moveable field of view through window (26), where the field of view has a center that defines a line of sight (LS). Line of sight (LS) pivots with swing prism (32) about pivot axis (A1); and defines a viewing angle relative to shaft axis (A). An elongate actuating link (34) is coupled with a side portion of swing prism (32) and extends proximally through endoscope shaft (14) to body (12). Actuating link (34) is configured to slide longitudinally within shaft (14) to thereby pivot swing prism (32) about pivot axis (A1) between a first end pivot position and a second end pivot position to adjust a direction of the line of sight (LS). A biasing spring (36) is coupled with swing prism (32) and may be configured to bias swing prism (32) toward an intermediate pivot position between the first and second end pivot positions. As described in greater detail below, actuating link (34) is configured to be moved by an automated drive mechanism, and optionally also by a surgeon via manual manipulation of features arranged on body (12).

As shown in FIG. 3, in which shaft axis (A) is represented by a zero angle, swing prism (32) may be mounted and pivotable about pivot axis (A1) such that the line of sight (LS) may pivot relative to shaft axis (A) from approximately −5 degrees to approximately 150 degrees; from approximately 0 degrees to approximately 120 degrees; from approximately 10 degrees to approximately 90 degrees; or any other suitable range. In the present example, swing prism (32) and window (26) provide a field of view that spans approximately 60 degrees. Accordingly, in various examples, the field of view of endoscope (10) may enable a viewing range that spans approximately 180 degrees, approximately 140 degrees, or any other suitable viewing range based on the pivot range of swing prism (32).

As shown in FIG. 2, distal shaft end (16) of endoscope (10) further includes a plurality of navigation sensors (40, 42) operable to communicate with IGS components of surgical navigation system (100), described below, to track a location and a rotational orientation of distal shaft end (16) within a patient during a surgical procedure. In particular, distal shaft end (16) of the present example includes a first navigation sensor (40) in the form of a first electrically conductive coil (e.g., a first metallic wire wrapped helically into a coil configuration), and a second navigation sensor (42) in the form of a second electrically conductive coil (e.g., a second metallic wire wrapped helically into a coil configuration). First sensor coil (40) is positioned about and coaxially with shaft axis (A) so as to encircle a distal portion of optical conduit (28). Second sensor coil (42) is positioned about a second axis (A2) that extends transversely to shaft axis (A); and is spaced radially from shaft axis (A) near an inner wall of distal shaft end (16) in the present example. Accordingly, first and second sensor coils (40, 42) are positioned about respective axes (A, A2) that are angled relative to one another such that axes (A, A2) are neither coaxial with nor parallel to one another. Further, first and second sensor coils (40, 42) are axially spaced from one another such that no portions of either sensor coil (40, 42) overlap one another. In the present example, second sensor coil (42) is arranged distally of first sensor coil (40) and proximally of self-focusing lens (30), though alternative arrangements may be provided in other examples.

As described in greater detail below, the configuration of navigation sensors (40, 42) described above enables precise tracking of a position and a rotational orientation of distal shaft end (16) as endoscope (10) is advanced through an alternating electromagnetic field generated about a patient. However, it will be appreciated that first and second sensors (40, 42) may be arranged in various other configurations in which sensors (40, 42) are positioned about respective axes that are angled relative to one another so as to achieve the same position tracking benefits described above. For instance, first navigation sensor (40) may be positioned about an axis that extends obliquely relative to shaft axis (A), for example as disclosed in U.S. patent application Ser. No. 15/923,164, entitled "Navigation Instrument With Obliquely Oriented Sensing Coil," filed Mar. 19, 2018, published as U.S. Pat. Pub. No. 2019/0282306 on Sep. 19, 2019, the disclosure of which is incorporated by reference herein. Additionally, second navigation sensor (42) may be omitted in some versions. In other versions, three or more navigation sensors may be provided. For instance, in some such variations, swing prism (32) may be provided with its own navigation sensor configured to indicate an angular orientation of swing prism (32), and thus line of sight (LS). Moreover, it will be appreciated that various other suitable types of navigation sensors other than conductive coils (40, 42) may be employed to track a location and a rotational orientation of distal shaft end (16) within a patient.

As shown in FIG. 2, a first signal transmission wire (44) extends longitudinally through shaft (14) and couples at its distal end with first navigation sensor (40). First signal transmission wire (44) couples at its proximal end with a component that places first sensor (40) in communication with a processor (108) of surgical navigation system (100), described in greater detail below. Similarly, a second signal transmission wire (46) extends longitudinally through shaft (14) and couples at its distal end with second navigation sensor (46), and at its proximal end with a component that places second sensor (42) in communication with system processor (108). Signal transmission wires (44, 46) are configured to transmit signals generated by navigation sensors (40, 42) proximally to system processor (108) to inform of a location and rotational orientation of endoscope (10) within a patient, as described below.

Figure 4:
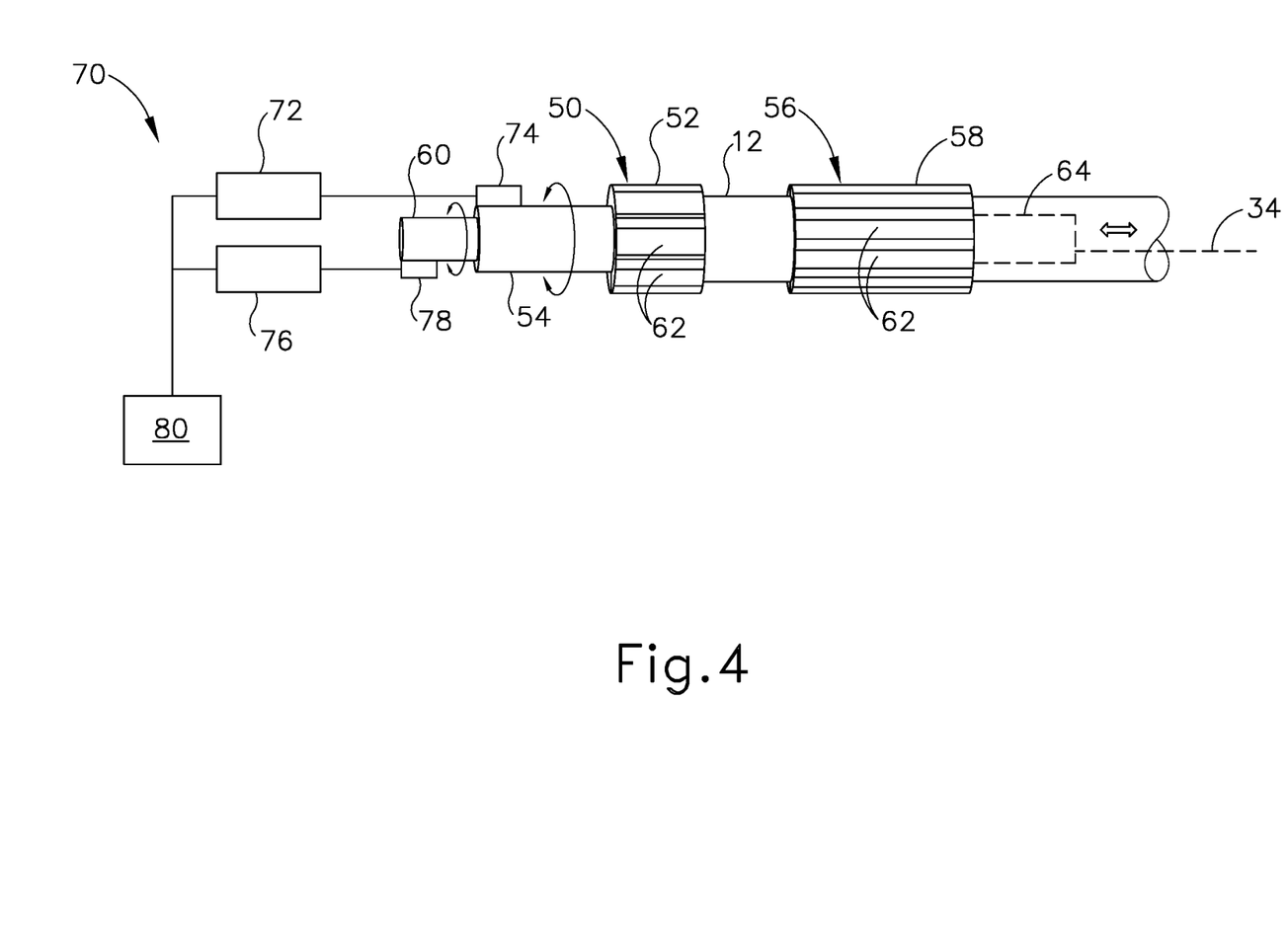
FIG. 4 depicts a schematic side elevational view of a proximal end portion of the endoscope of FIG. 1, schematically showing a drive mechanism having first and second actuators and a controller operable to control the actuators.

FIG. 4 shows additional features of endoscope (10) that facilitate manipulation of swing prism (32) for adjusting the direction of line of sight (LS) during a surgical procedure. Endoscope (10) includes a first rotation dial (50) arranged at a proximal end of body (12) and having a first dial knob (52) and a first dial shaft (54) that extends proximally from first dial knob (52). First rotation dial (50) is rotatably coupled with a proximal end of body (12) and is rotationally fixed with endoscope shaft (14) such that rotation of first rotation dial (50) relative to body (12) about shaft axis (A) drives rotation of shaft (14) relative to body (12) about shaft axis (A). Rotation of shaft (14) relative to body (12) causes swing prism (32), and thus line of sight (LS), to rotate relative to body (12) about shaft axis (A).

Endoscope (10) further includes a second rotation dial (56) rotatably coupled with body (12) distally of first rotation dial (50). Second rotation dial (56) has a second dial knob (58) and a second dial shaft (60) that extends proximally from second dial knob (58). In the present example, first and second rotation dials (50, 56) are arranged coaxially about shaft axis (A) such that second dial shaft (60) extends proximally through a central lumen of first rotation dial (50), along shaft axis (A). Additionally, an exposed proximal end of second dial shaft (60) extends proximally beyond a proximal end of first dial shaft (54). Each rotation dial (50, 56) includes ridges (62) on its respective dial knob (52, 58) that facilitate manual rotation of dials (50, 56) by a surgeon for selective positioning of swing prism (32) and its line of sight (LS). Though not shown, rotation dial knobs (52, 58) and/or endoscope body (12) may further include visual indicia or like features that indicate rotational positions of rotation dials (50, 56).

Second rotation dial (56) is coupled with an internal coupling member (64) housed within body (12), which is coupled with a proximal end of actuating link (34). Various suitable configurations of coupling member (64) will be apparent to those of ordinary skill in the art in view of the teachings herein. By way of example only, coupling member (64) and the proximal end of actuating link (34) may be coupled via complementary helical threading. Coupling member (64) may be operable as a camming member such that rotation of second rotation dial (56) relative to body (12) drives proximal and distal translation of actuating link (34) along shaft axis (A), via coupling member (64). Accordingly, rotation of second rotation dial (56) relative to body (12) in a first direction about shaft axis (A) causes swing prism (32) and line of sight (LS) to pivot relative to shaft (14) in a first direction about pivot axis (A1). Further, rotation of second rotation dial (56) relative to body (12) in a second direction about shaft axis (A) causes swing prism (32) and line of sight (LS) to pivot relative to shaft (14) in a second direction about pivot axis (A1). Thus, first and second rotation dials (50, 56) may be selectively rotated relative to body (12) to achieve a desired rotational orientation of line of sight (LS) about shaft axis (A), via first rotation dial (50); and a desired angular orientation of line of sight (LS) relative to shaft axis (A), via second rotation dial (56). In this manner, line of sight (LS) may be suitably directed toward a selected point of interest, as described in greater detail below.

As shown in FIG. 4, endoscope (10) further includes a drive mechanism (70) operatively coupled with rotation dials (50, 56) to provide automated positioning of swing prism (32) about and relative to shaft axis (A). Drive mechanism (70) of the present example includes a first actuator in the form of a first electric motor (72) having a first drive shaft engaged with first dial shaft (54) via a first drive coupling (74). Drive mechanism (70) further includes a second actuator in the form of a second electric motor (76) having a second drive shaft engaged with second dial shaft (60) via a second drive coupling (78). First motor (72) is operable to rotate first rotation dial (50) relative to body (12) to thereby rotate endoscope shaft (14) relative to body (12) about shaft axis (A). Second motor (76) is operable to rotate second rotation dial (56) relative to body (12) to pivot swing prism (32) relative to shaft (14) about pivot axis (A1).

Motors (72, 76) may comprise stepper motors, for instance, and drive couplings (74, 78) may comprise gear members, for instance. In other examples, actuators (72, 76) may be of various other suitable types readily apparent to those of ordinary skill in the art. Drive mechanism (70) may be housed within a housing (not shown) coupled directly to endoscope body (12). Alternatively, one or more components of drive mechanism (70) may be housed remotely from body (12).

Figure 6:
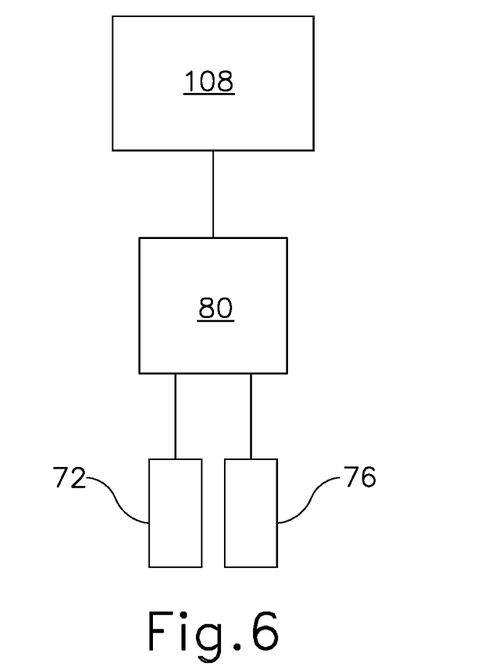
FIG. 6 depicts a schematic view of select components of the surgical navigation system of FIG. 5, including a processor and the drive mechanism controller and actuators of FIG. 4.

Drive mechanism motors (72, 76) are in communication with a motor controller (80), which is operable to control activation of motors (72, 76) in response to instructions provided by a processor (108) of surgical navigation system (100), as shown in FIG. 6 and as described in greater detail below. Each motor (72, 76) may be provided with an encoder (not shown) that communicates to processor (108) a present positional state of motor (72, 76). Such encoders may thus enable system (100) to monitor a rotational position of endoscope shaft (14) about shaft axis (A) relative to body (12), and an angular orientation of swing prism (32) and line of sight (LS) about pivot axis (A1) relative to shaft axis (A). When controlled by motor controller (80), motors (72, 76) provide automated positioning of swing prism (32) and thus line of sight (LS) during a surgical procedure, as described below in connection with FIG. 7.

Endoscope (10) may be further configured in accordance with one or more teachings of U.S. Pat. No. 9,808,144, entitled "Swing Prism Endoscope," issued Nov. 7, 2017, the disclosure of which is incorporated by reference herein; and/or U.S. Pat. Pub. No. 2010/0030031, now abandoned, entitled "Swing Prism Endoscope," incorporated by reference above.

B. IGS Features of Surgical Navigational System

Figure 5:
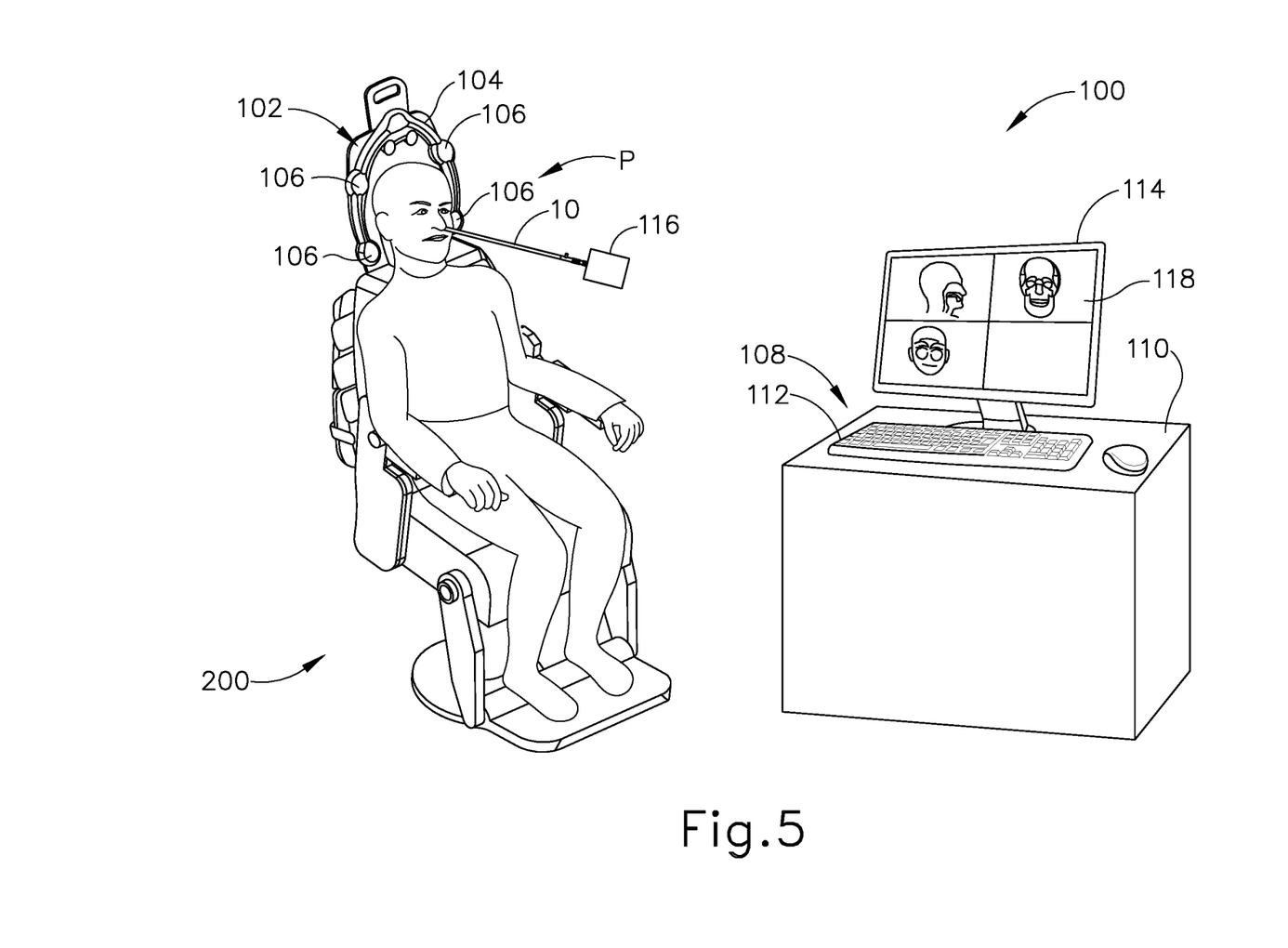
FIG. 5 depicts a schematic perspective view of an exemplary surgical navigation system that incorporates the endoscope of FIG. 1.

FIG. 5 shows surgical navigation system (100), which incorporates automatically driven endoscope (10) described above, and various additional image-guided surgery (IGS) features, described below. Surgical navigation system (100) is configured to implement navigation sensors (40, 42) of endoscope (10) to provide real-time location tracking of distal shaft end (16) within a patient (P) during a surgical procedure, and automated positioning of swing prism (32) so that line of sight (LS) is directed toward a selected point of interest identified by the surgeon. Though not shown, surgical navigation system (100) may further include one or more additional surgical instruments each equipped with one or more navigation sensors similar to sensors (40, 42) described above.

The IGS component of surgical navigation system (100) includes a field generator assembly (102), which comprises a set of electromagnetic field generators (106) that are integrated within a horseshoe-shaped frame (104) configured to be positioned about the head (H) of patient (P). Field generators (106) are operable to generate alternating magnetic fields of different frequencies around the patient's head (H). Field generators (106) thereby enable tracking of the position of a navigation instrument, such as endoscope (10), that is inserted into the patient's head (H). Various suitable components that may be used to form and drive field generators (106) will be apparent to those of ordinary skill in the art in view of the teachings herein.

In the present example, frame (104) is mounted to the headrest of a chair (200), with patient (P) being seated in chair (200) such that frame (104) partially surrounds the patient's head (H). By way of example only, chair (200) and/or field generator assembly (102) may be configured and operable in accordance with at least some of the teachings of U.S. patent application Ser. No. 15/933,737, entitled "Apparatus to Secure Field Generating Device to Chair," filed Mar. 23, 2018, issued as U.S. Pat. No. 10,561,370 on Feb. 18, 2020, the disclosure of which is incorporated by reference herein. In other examples, patient (P) may be supported on a variety of other suitable support structures, such as a medical procedure table. Frame (104) may be supported by the patient support structure or by an independent structure positioned adjacent to the patient support structure. In other examples, frame (104) may be secured directly to the patient's head (H).

Navigation sensors (40, 42), provided in in the form of electrically conductive sensor coils as described above, are configured to interact with the electromagnetic field generated by field generators (106) to generate electric signals. Specifically, the presence of navigation sensors (40, 42) in the alternating magnetic field induces an electrical current in each sensor (40, 42), which is communicated as an electric signal proximally through signal transmission wires (44, 46) to a processor (108) of surgical navigation system (100). Processor (108) receives the signals and executes an algorithm to determine a location of the respective navigation sensor (40, 42) within a three-dimensional space occupied by the alternating electromagnetic field, which surrounds head (H) of patient (P) in the present example. Processor (108) correlates this three-dimensional space to the known anatomy of patient (P), analyzed preoperatively, and determines the three-dimensional locations of sensors (40, 42) with patient (P). As described above, navigation sensors (40, 42) of the present example are arranged adjacent to one another within distal shaft end (16). Thus, each sensor (40, 42) is independently suitable to indicate a location of distal shaft end (16) within patient (P). In other examples, navigation sensors (40, 42) may be spaced apart from one another along shaft axis (A) so that each sensor (40, 42) indicates the present location of a respective portion of endoscope (10) within patient (P).

As described above, first and second navigation sensors (40, 42) are positioned about respective axes (A, A2) that are angled relative to one another, and second sensor (42) is radially offset from shaft axis (A) within distal shaft end (16). Accordingly, the signals provided by second sensor (42) enable processor (16) to determine a rotational orientation of endoscope shaft (14), and thus line of sight (LS), about shaft axis (A) within the three-dimensional space. As described above, it will be appreciated that second navigation sensor (42) may be omitted in some versions, including versions in which first navigation sensor (40) is positioned about an axis that extends obliquely relative to shaft axis (A).

As described above, system (100) may monitor the rotational orientation of shaft (14) relative to body (12) via an encoder coupled with first motor (72) of drive mechanism (70). A second encoder may be coupled with second motor (76) to enable system (100) to monitor an angular orientation of swing prism (32), and thus line of sight (LS), about pivot axis (A1). As described below in connection with FIGS. 6 and 7, processor (108) references these known rotational and angular orientations of swing prism (32) and line of sight (LS), along with the three-dimensional location of distal shaft end (16) within patient (P), when generating suitable commands to direct line of sight (LS) toward a point of interest within patient (P) specified by the surgeon.

Processor (108) of surgical navigation system (100) comprises a processing unit that communicates with one or more memories and is configured to control field generators (106) and other elements of navigation system (100). In the present example, processor (108) is mounted in a console (110), which comprises operating controls (112) that include a keypad and/or a pointing device such as a mouse or trackball. A physician uses operating controls (112) to interact with processor (108) while performing the surgical procedure. Processor (108) uses software stored in a memory of processor (108) to calibrate and operate system (100). Such operation includes driving field generators (106), processing data received from navigation sensors (40, 42), processing data from operating controls (112), and driving a display (114). The software may be downloaded to processor (108) in electronic form, over a network, for example, or it may, alternatively or additionally, be provided and/or stored on non-transitory tangible media, such as magnetic, optical, or electronic memory.

Navigation sensors (40, 42) of endoscope (10) communicate with processor (108) via a communication unit (116) that is coupled with a proximal end of endoscope (10), as shown in FIG. 5, and connects with the proximal ends of signal transmission wires (44, 46). Communication unit (116) of the present example is configured to provide wireless communication of data and other signals between console (110) and navigation sensors (40, 42). In some versions, communication unit (116) simply communicates data or other signals from navigation sensors (40, 42) to console (110) uni-directionally, without also communicating data or other signals from console (110). In some other versions, communication unit (116) provides bi-directional communication of data or other signals between navigation sensors (40, 42) and console (110). While communication unit (116) of the present example couples with console (110) wirelessly, some other versions may provide wired coupling between communication unit (116) and console (110). Various other suitable features and functionality that may be incorporated into communication unit (116) will be apparent to those of ordinary skill in the art in view of the teachings herein.

System display (114) is operable to depict a navigation image (118) that shows the real-time position of distal shaft end (16) of endoscope (10) in relation to anatomy of patient (P). The anatomy may be presented by navigation image (118) in the form of a video camera image, a CT scan image, and/or a computer generated three-dimensional model of the anatomy, which may be displayed simultaneously and/or superimposed on each other, for instance. In addition to the anatomy image, navigation image (118) shows a graphical representation of endoscope (10) and any other surgical instruments inserted into patient (P) that have an IGS navigation sensor similar to sensors (40, 42) described above. This graphical representation is superimposed on the anatomy image and enables the physician to identify the position of distal shaft end (16) of endoscope (10) relative to adjacent anatomical features of patient (P) in real-time during a surgical procedure. The one or more graphical representations shown by navigation image (118) may look like the respective surgical instrument, such as endoscope (10), or they may be a much simpler representation such as a dot, crosshairs, etc.

By way of example only, display (114) may depict navigation image (118) in accordance with at least some of the teachings of U.S. Pat. Pub. No. 2016/0008083, entitled "Guidewire Navigation for Sinuplasty," published Jan. 14, 2016, issued as U.S. Pat. No. 10,463,242 on Nov. 5, 2019, the disclosure of which is incorporated by reference herein. In some instances, system display (114) may depict navigation image (118) simultaneously with an endoscopic image provided by endoscope (10). Accordingly, the images provided through display (114) may assist the physician in maneuvering and otherwise manipulating endoscope (10) and any additional surgical instruments within patient (P).

Any suitable device may be used to generate a three-dimensional model of the internal anatomy of the portion of patient (P) (e.g., head (H)) about which the electromagnetic field is generated and into which endoscope (10) is inserted during a surgical procedure. By way of example only, such a model may be generated in accordance with at least some of the teachings of U.S. Pat. Pub. No. 2016/0310042, entitled "System and Method to Map Structures of Nasal Cavity," published Oct. 27, 2016, issued as U.S. Pat. No. 10,362,965 on Jul. 30, 2019, the disclosure of which is incorporated by reference herein. Still other suitable ways in which a three-dimensional anatomical model may be generated will be apparent to those of ordinary skill in the art in view of the teachings herein. It should also be understood that, regardless of how or where the three-dimensional model is generated, the model may be stored on console (110). Console (110) may thus render images of at least a portion of the model via display (114), and further render real-time video images of the position of distal shaft end (16) of endoscope (10) in relation to the model via display (114).

In various examples, the IGS components of surgical navigation system may be further configured in accordance with one or more teachings of U.S. patent application Ser. No. 15/695,520, entitled "Sensor Guided Instrument with Penetrating Feature," filed Sep. 5, 2017, issued as U.S. Pat. No. 10,835,327 on Nov. 17, 2020; U.S. patent application Ser. No. 15/797,049, entitled "Dilation Catheter with Navigation Sensor and Vent Passageway in Tip," filed Oct. 30, 2017, issued as U.S. Pat. No. 10,736,647 on Aug. 11, 2020; U.S. Pat. No. 8,702,626, entitled "Guidewires for Performing Image Guided Procedures," issued Apr. 22, 2014; U.S. Pat. No. 8,320,711, entitled "Anatomical Modeling from a 3-D Image and a Surface Mapping," issued Nov. 27, 2012; U.S. Pat. No. 8,190,389, entitled "Adapter for Attaching Electromagnetic Image Guidance Components to a Medical Device," issued May 29, 2012; U.S. Pat. No. 8,123,722, entitled "Devices, Systems and Methods for Treating Disorders of the Ear, Nose and Throat," issued Feb. 28, 2012; U.S. Pat. No. 7,720,521, entitled "Methods and Devices for Performing Procedures within the Ear, Nose, Throat and Paranasal Sinuses," issued May 18, 2010; U.S. Pat. Pub. No. 2014/0364725, entitled "Systems and Methods for Performing Image Guided Procedures within the Ear, Nose, Throat and Paranasal Sinuses," published Dec. 11, 2014, now abandoned; U.S. Pat. Pub. No. 2014/0200444, entitled "Guidewires for Performing Image Guided Procedures," published Jul. 17, 2014, now abandoned; U.S. Pat. No. 9,198,736, entitled "Adapter for Attaching Electromagnetic Image Guidance Components to a Medical Device," issued Dec. 1, 2015; U.S. Pat. Pub. No. 2011/0060214, entitled "Systems and Methods for Performing Image Guided Procedures within the Ear, Nose, Throat and Paranasal Sinuses," published Mar. 10, 2011, now abandoned; U.S. Pat. No. 9,167,961, entitled "Methods and Apparatus for Treating Disorders of the Ear Nose and Throat," issued Oct. 27, 2015; and/or U.S. Pat. Pub. No. 2007/0208252, entitled "Systems and Methods for Performing Image Guided Procedures within the Ear, Nose, Throat and Paranasal Sinuses," published Sep. 6, 2007, now abandoned. The disclosure of each of these references is incorporated by reference herein.

C. Automated Positioning of Endoscope Swing Prism for Viewing Selected Anatomical Feature As described above, in some instances during a surgical procedure the surgeon may desire to precisely direct the endoscope line of sight (LS) toward a particular anatomical feature within patient (P) to view the feature endoscopically. As described below, the various components of surgical navigation system (100) described above enable the surgeon to identify and select the particular anatomical feature via system display (114), and system (100) will then automatically orient swing prism (32) so that its line of sight (LS) is directed toward the anatomical feature for endoscopic viewing.

Figure 7:
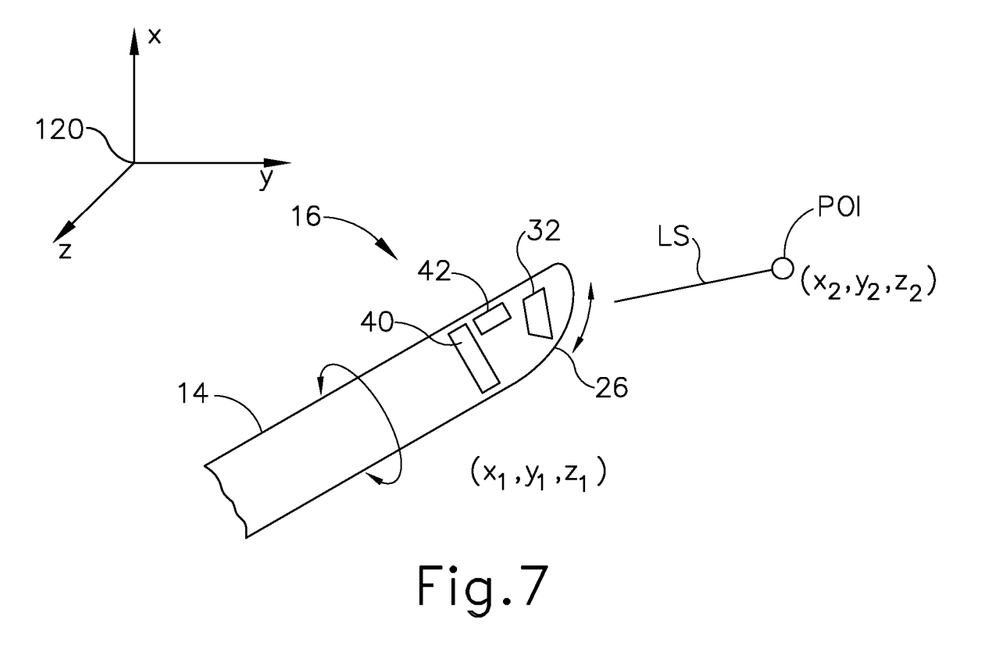
FIG. 7 depicts a schematic side view of the endoscope of FIG. 1 operating within a three-dimensional coordinate system, showing a line of sight of the endoscope being oriented toward a selected point of interest within the coordinate system.

As shown in FIG. 7, endoscope (10) is inserted into patient (P) such that distal shaft end (16) is positioned within a three-dimensional space occupied by an electromagnetic field generated by field generators (106), described above. Processor (108) associates the space with a three-dimensional coordinate system (120) and correlates the anatomical features of patient (P) located within the space with coordinate system (120). Processor (108) tracks a location of distal shaft end (16) within coordinate system (120), represented by point $(x_1, y_1, z_1)$ shown in FIG. 7, and graphically displays this location relative to the anatomical features of patient (P) in real-time via navigation image (118) of display (114), as generally described above. Signals generated by first navigation sensor (40) of endoscope (10) may indicate the location of distal shaft end (16) within coordinate system (120), while signals generated by second navigation sensor (42) may indicate a rotational orientation of endoscope shaft (14), and thus swing prism (32), within coordinate system (120), as also generally described above.

During the surgical procedure shown in FIG. 7, a surgeon may identify a particular anatomical feature shown by navigation image (118) on display (114) that the surgeon wishes to view endoscopically with endoscope (10). Using display (114), with or without operating controls (112), the surgeon may select the anatomical feature on navigation image (118) such that processor (108) recognizes the selected point as a point of interest (POI) having coordinates $(x_2, y_2, z_2)$ within coordinate system (120). Processor (108) then compares the location of distal shaft end (16) within coordinate system (120) to the location of point of interest (POI) within coordinate system (120). Simultaneously, processor (108) determines a rotational orientation of endoscope shaft (14) within coordinate system (120), via signals received from second navigation sensor (42), and compares this rotational orientation to the location of point of interest (POI). Processor (108) also determines an angular orientation of swing prism (32) and line of sight (LS) about pivot axis (A1), relative to shaft axis (A), via an encoder coupled with second motor (76). In other examples, sensing features of various other suitable types readily apparent to those of ordinary skill in the art may be used in place of an encoder to detect an angular orientation of swing prism (32) about pivot axis (A1).

With the detected information described above, processor (108) executes an algorithm to determine the requisite rotational orientation of endoscope shaft (14) about shaft axis (A), and the requisite angular orientation of swing prism (32) about pivot axis (A1), needed to direct line of sight (LS) toward point of interest (POI) within coordinate system (120). Based on the results of this algorithm, processor (108) generates and transmits suitable commands to motor controller (80). Motor controller (80) executes these commands to activate first motor (72) and/or second motor (76) to rotate shaft (14) relative to body (12) about shaft axis (A), and/or to pivot swing prism (32) relative to shaft (14) about pivot axis (A1), so that line of sight (LS) is directed toward point of interest (POI). With line of sight (LS) directed toward point of interest (POI), the surgeon is able to view the anatomical feature corresponding to point of interest (POI) endoscopically. Should the surgeon wish to view another anatomical feature within patient (P), the surgeon may select the anatomical feature on display (114) and system (100) may execute the same steps described above to direct line of sight (LS) toward the new point of interest (POI). In this manner, surgical navigation system (10) implements an automated directional process that enables surgeon to ensure that endoscope swing prism (32) is precisely oriented so that the endoscopic image shows a desired anatomical feature of patient (P).

II. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical navigation system, comprising: (a) an endoscope, wherein the endoscope comprises: (i) a body, (ii) a shaft extending distally from the body and having a distal shaft end, (iii) an optical conduit extending distally through the shaft, wherein the optical conduit is operable to optically transmit an image, and (iv) a moveable optical element arranged at the distal shaft end, wherein the movable optical element is configured to provide a field of view defining a line of sight, wherein the moveable optical element is operable to capture an image within the field of view and transmit the image proximally to the optical conduit to enable visualization of the image by a user; (b) a drive mechanism coupled with the endoscope, wherein the drive mechanism is operable to move the movable optical element relative to the shaft to adjust a direction of the line of sight; (c) a navigation sensor operatively associated with the endoscope, wherein the navigation sensor is operable to generate a signal corresponding to a location of the distal shaft end within a patient; and (d) a processor, wherein the processor is in communication with the navigation sensor and with the drive mechanism, wherein the processor is operable to determine a location of the distal shaft end within the patient based on the signal received from the navigation sensor, wherein the processor is further operable to command the drive mechanism to position the movable optical element so that the line of sight is directed toward a selected point of interest within the patient.

Example 2

The surgical navigation system of Example 1, wherein the shaft is rigid.

Example 3

The surgical navigation system of any of the preceding Examples, wherein the endoscope further comprises a window arranged at the distal shaft end, wherein the endoscope is operable to capture the image through the window.

Example 4

The surgical navigation system of any of the preceding Examples, wherein the endoscope further comprises a lens, wherein the lens is arranged between the movable optical element and a distal end of the optical conduit.

Example 5

The surgical navigation system of any of the preceding Examples, wherein the moveable optical element is configured to pivot about a pivot axis that extends transversely to a longitudinal shaft axis.

Example 6

The surgical navigation system of Example 5, wherein the drive mechanism comprises a first actuator and a second actuator, wherein the first actuator is operable to rotate the movable optical element relative to the body about the shaft axis, wherein the second actuator is operable to pivot the movable optical element relative to the shaft about the pivot axis.

Example 7

The surgical navigation system of Example 6, wherein the shaft is rotatable relative to the body about the shaft axis, wherein the first actuator is operable to rotate the shaft relative to the body to thereby rotate the movable optical element and the field of view about the shaft axis.

Example 8

The surgical navigation system of any of Examples 6 through 7, wherein the first actuator comprises a first motor, wherein the second actuator comprises a second motor.

Example 9

The surgical navigation system of any of the preceding Examples, wherein the navigation sensor comprises an electromagnetic sensor.

Example 10

The surgical navigation system of any of the preceding Examples, wherein the navigation sensor comprises an electrically conductive coil.

Example 11

The surgical navigation system of any of the preceding Examples, wherein the surgical navigation system further comprises a display in communication with the processor, wherein the display is operable to depict a navigation image that shows in real-time the location of the shaft distal end relative to anatomy of the patient based on the signal provided by the navigation sensor.

Example 12

The surgical navigation system of Example 11, wherein the processor is operable to accept the point of interest as an input provided via the display, wherein the point of interest corresponds to an anatomical feature of the patient shown by the navigation image.

Example 13

The surgical navigation system of any of Examples 11 through 12, wherein the navigation image includes a computed tomography (CT) image.

Example 14

The surgical navigation system of any of Examples 11 through 13, wherein the navigation image includes a three-dimensional image, wherein the point of interest has coordinates that correspond to a three-dimensional coordinate system.

Example 15

The surgical navigation system of any of Examples 11 through 14, wherein the display is also in communication with the optical conduit of the endoscope, wherein the display is further operable to display the image captured by the endoscope.

Example 16

A surgical navigation system, comprising: (a) an endoscope, wherein the endoscope comprises: (i) a body, (ii) a shaft extending distally from the body along a longitudinal shaft axis, wherein the shaft includes a distal shaft end, (iii) an optical conduit extending distally through the shaft, wherein the optical conduit is operable to optically transmit an image, and (iv) a moveable optical element arranged at the distal shaft end, wherein the movable optical element is configured to pivot about a pivot axis that extends transversely to the shaft axis, wherein the movable optical element is configured to provide a field of view defining a line of sight, wherein the moveable optical element is operable to capture an image within the field of view and transmit the image proximally to the optical conduit to enable visualization of the image by a user; and (b) a drive mechanism coupled with the endoscope, wherein the drive mechanism is operable to move the movable optical element relative to the shaft to adjust a direction of the line of sight, wherein the drive mechanism comprises: (i) a first actuator, wherein the first actuator is operable to rotate the movable optical element relative to the body about the shaft axis, and (ii) a second actuator, wherein the second actuator is operable to pivot the movable optical element relative to the shaft about the pivot axis.

Example 17

The surgical navigation system of Example 16, further comprising a processor, wherein the processor is operable to control the first and second actuators to position the movable optical element so that the line of sight is directed toward a selected point of interest within a coordinate system.

Example 18

The surgical navigation system of any of Examples 16 through 17, further comprising a navigation sensor operatively associated with the endoscope, wherein the navigation sensor is operable to transmit to the processor a signal corresponding to a location of the distal shaft end within the coordinate system, wherein the processor is operable to control the first and second actuators based on the signal.

Example 19

A method of operating a surgical navigation system during a surgical procedure on a patient, wherein the surgical navigation system includes an endoscope having a moveable optical element that provides a field of view defining a line of sight, wherein the surgical navigation system further includes a drive mechanism operatively coupled with the endoscope, the method comprising: (a) depicting a navigation image on a display of the surgical navigation system, wherein the navigation image shows in real-time a location of a distal end of the endoscope relative to anatomy of the patient; (b) receiving user input via the display, wherein the user input specifies a point of interest that corresponds to an anatomical feature of the patient shown by the navigation image; (c) with a processor, comparing the location of the distal end of the endoscope to the point of interest specified by the user input; and (d) based on the comparison, controlling the drive mechanism with the processor to move the movable optical element to a position in which the line of sight is directed toward the point of interest specified by the user input.

Example 20

The method of Example 19, wherein the endoscope includes a longitudinal axis, wherein the method further comprises determining with the processor a rotational orientation of the endoscope relative to the point of interest about the longitudinal axis, wherein the step of controlling the drive mechanism is further based on the determination of the rotational orientation.

Example 21

The method of any of Examples 19 through 20 wherein controlling the drive mechanism to move the moveable optical element comprises rotating the moveable optical element about a first axis and pivoting the moveable optical element about a second axis that extends transversely to the first axis.

III. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical navigation system, comprising:
   (a) an endoscope, wherein the endoscope comprises:
      (i) a body,
      (ii) a shaft extending distally from the body along a longitudinal shaft axis and having a distal shaft end,
      (iii) an optical conduit extending distally through the shaft, wherein the optical conduit is operable to optically transmit an image, and (iv) a moveable optical element arranged at the distal shaft end, wherein the movable optical element is configured to provide a field of view defining a line of sight, wherein the moveable optical element is operable to capture an image within the field of view and transmit the image proximally to the optical conduit to enable visualization of the image by a user;

(b) a drive mechanism coupled with the endoscope, wherein the drive mechanism is operable to move the movable optical element relative to the shaft to adjust a direction of the line of sight;

(c) at least one navigation sensor operatively associated with the endoscope, wherein the at least one navigation sensor is operable to generate a signal corresponding to a location of the distal shaft end within a patient, wherein the at least one navigation sensor is positioned on the distal shaft end; and (d) a processor, wherein the processor is in communication with the at least one navigation sensor and with the drive mechanism, wherein the processor is operable to determine a location of the distal shaft end within the patient based on the signal received from the at least one navigation sensor, wherein the processor is further operable to command the drive mechanism to position the movable optical element so that the line of sight is directed toward a selected point of interest within the patient, wherein the at least one navigation sensor includes a first navigation sensor positioned about the shaft axis such that the first navigation sensor encircles a portion of the optical conduit, and wherein the at least one navigation sensor includes a second navigation sensor positioned about a second axis extending transversely to the shaft axis, wherein the second navigation sensor is entirely spaced radially outwardly from the shaft axis.

2. The surgical navigation system of claim 1, wherein the shaft is rigid.

3. The surgical navigation system of claim 1, wherein the endoscope further comprises a window arranged at the distal shaft end, wherein the endoscope is operable to capture the image through the window.

4. The surgical navigation system of claim 1, wherein the endoscope further comprises a lens, wherein the lens is arranged between the movable optical element and a distal end of the optical conduit.

5. The surgical navigation system of claim 1, wherein the moveable optical element is configured to pivot about a pivot axis that extends transversely to the shaft axis.

6. The surgical navigation system of claim 5, wherein the drive mechanism comprises a first actuator and a second actuator, wherein the first actuator is operable to rotate the movable optical element relative to the body about the shaft axis, wherein the second actuator is operable to pivot the movable optical element relative to the shaft about the pivot axis.

7. The surgical navigation system of claim 6, wherein the shaft is rotatable relative to the body about the shaft axis, wherein the first actuator is operable to rotate the shaft relative to the body to thereby rotate the movable optical element and the field of view about the shaft axis.

8. The surgical navigation system of claim 6, wherein the first actuator comprises a first motor, wherein the second actuator comprises a second motor.

9. The surgical navigation system of claim 1, wherein the at least one navigation sensor comprises an electromagnetic sensor.

10. The surgical navigation system of claim 9, wherein the electromagnetic sensor comprises an electrically conductive coil.

11. The surgical navigation system of claim 1, wherein the surgical navigation system further comprises a display in communication with the processor, wherein the display is operable to depict a navigation image that shows in real-time the location of the shaft distal end relative to anatomy of the patient based on the signal provided by the at least one navigation sensor.

12. The surgical navigation system of claim 11, wherein the processor is operable to accept the point of interest as an input provided via the display, wherein the point of interest corresponds to an anatomical feature of the patient shown by the navigation image.

13. The surgical navigation system of claim 11, wherein the navigation image includes a three-dimensional image, wherein the point of interest has coordinates that correspond to a three-dimensional coordinate system.

14. The surgical navigation system of claim 1, wherein the first and second navigation sensors are spaced apart from each other in a direction in which the shaft axis extends.

15. The surgical navigation system of claim 1, wherein the first navigation sensor is operable to generate a signal corresponding to a location of the distal shaft end within a coordinate system, wherein the second navigation sensor is operable to generate a signal corresponding to a rotational orientation of the shaft within the coordinate system.

16. A surgical navigation system, comprising:

(a) an endoscope, wherein the endoscope comprises:
  (i) a body,
  (ii) a shaft extending distally from the body along a longitudinal shaft axis, wherein the shaft includes a distal shaft end,
  (iii) an optical conduit extending distally through the shaft, wherein the optical conduit is operable to optically transmit an image, and
  (iv) a moveable optical element arranged at the distal shaft end, wherein the movable optical element is configured to pivot about a pivot axis that extends transversely to the shaft axis, wherein the movable optical element is configured to provide a field of view defining a line of sight, wherein the moveable optical element is operable to capture an image within the field of view and transmit the image proximally to the optical conduit to enable visualization of the image by a user;

(b) a drive mechanism coupled with the endoscope, wherein the drive mechanism is operable to move the movable optical element relative to the shaft to adjust a direction of the line of sight, wherein the drive mechanism comprises:
  (i) a first actuator, wherein the first actuator is operable to rotate the movable optical element relative to the body about the shaft axis, and
  (ii) a second actuator, wherein the second actuator is operable to pivot the movable optical element relative to the shaft about the pivot axis;

(c) a processor, wherein the processor is operable to control the first and second actuators to position the movable optical element so that the line of sight is directed toward a selected point of interest within a coordinate system; and (d) at least one navigation sensor operatively associated with the endoscope, wherein the at least one navigation sensor is operable to transmit to the processor a signal corresponding to a location of the distal shaft end within the coordinate system, wherein the processor is operable to control the first and second actuators based on the signal, wherein the at least one navigation sensor is positioned on the distal shaft end, wherein the at least one navigation sensor includes a first navigation sensor positioned about the longitudinal shaft axis such that the first navigation sensor encircles a portion of the optical conduit, and wherein the at least one navigation sensor includes a second navigation sensor positioned about a second axis extending transversely to the shaft axis, wherein the second navigation sensor is entirely spaced radially outwardly from the shaft axis.

17. The surgical navigation system of claim 16, wherein the first and second navigation sensors are spaced apart from each other in a direction in which the shaft axis extends.

18. A method of operating a surgical navigation system during a surgical procedure on a patient, wherein the surgical navigation system includes an endoscope having a moveable optical element that provides a field of view defining a line of sight, wherein the endoscope includes a longitudinal axis, wherein the surgical navigation system further includes a drive mechanism operatively coupled with the endoscope, the method comprising:

(a) inserting a distal end of the endoscope into a nasal passageway of the patient, the distal end including first and second navigation sensors, wherein the first navigation sensor is positioned about the longitudinal axis, wherein the second navigation sensor is entirely spaced radially outwardly from the longitudinal axis, wherein the first navigation sensor is operable to generate a first signal corresponding to a location of the distal end relative to anatomy of the patient, wherein the second navigation sensor is operable to generate a second signal corresponding to a rotational orientation of the endoscope relative to a point of interest about the longitudinal axis, wherein the first navigation sensor is operable to generate a first signal corresponding to a location of the distal end relative to anatomy of the patient, wherein the second navigation sensor is operable to generate a second signal corresponding to a rotational orientation of the endoscope relative to a point of interest about the longitudinal axis;

(b) after the act of inserting the distal end of the endoscope into the nasal passageway of the patient, depicting a navigation image on a display of the surgical navigation system, wherein the navigation image shows in real-time the location of the distal end of the endoscope relative to anatomy of the patient;

(c) receiving user input via the display, wherein the user input specifies the point of interest that corresponds to an anatomical feature of the patient shown by the navigation image;

(d) with a processor, comparing the location of the distal end of the endoscope to the point of interest specified by the user input;

(e) based on the comparison, controlling the drive mechanism with the processor to move the movable optical element to a position in which the line of sight is directed toward the point of interest specified by the user input; and (f) determining with the processor the rotational orientation of the endoscope relative to the point of interest about the longitudinal axis, wherein the step of controlling the drive mechanism is further based on the determination of the rotational orientation.

19. The method of claim 18, wherein the navigation image shows in real-time the location of the distal end of the endoscope relative to anatomy of the patient based on the first signal generated by the first navigation sensor.

20. The method of claim 19, wherein the act of determining with the processor the rotational orientation of the endoscope relative to the point of interest about the longitudinal axis is performed based on the second signal generated by the second navigation sensor.

* * * * *